United States Patent
Bloom et al.

(10) Patent No.: US 9,176,147 B2
(45) Date of Patent: Nov. 3, 2015

(54) DETECTION OF B-CELL ACTIVATING FACTOR AS A BIOMARKER FOR ANTIBODY MEDIATED REJECTION IN TRANSPLANT RECIPIENTS

(75) Inventors: Debra D. Bloom, Sun Prairie, WI (US);
Hans W. Sollinger, Madison, WI (US);
Arjang Djamali, Cross Plains, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/501,671

(22) PCT Filed: Oct. 25, 2010

(86) PCT No.: PCT/US2010/053967
§ 371 (c)(1),
(2), (4) Date: Jul. 2, 2012

(87) PCT Pub. No.: WO2011/059686
PCT Pub. Date: May 19, 2011

(65) Prior Publication Data
US 2012/0264142 A1    Oct. 18, 2012

Related U.S. Application Data

(60) Provisional application No. 61/255,953, filed on Oct. 29, 2009.

(51) Int. Cl.
*G01N 33/53* (2006.01)
*G01N 33/68* (2006.01)
*A61P 37/00* (2006.01)
*A61P 37/06* (2006.01)
*C07K 14/475* (2006.01)
*C07K 14/52* (2006.01)

(52) U.S. Cl.
CPC .......... *G01N 33/6893* (2013.01); *C07K 14/475* (2013.01); *C07K 14/52* (2013.01); *G01N 2800/245* (2013.01)

(58) Field of Classification Search
None
See application file for complete search history.

(56) References Cited

U.S. PATENT DOCUMENTS

| | | | |
|---|---|---|---|
| 4,582,788 A | 4/1986 | Erlich | |
| 4,683,195 A | 7/1987 | Mullis et al. | |
| 4,863,849 A | 9/1989 | Melamede | |
| 4,876,187 A | 10/1989 | Duck et al. | |
| 5,011,769 A | 4/1991 | Duck et al. | |
| 5,185,243 A | 2/1993 | Ullman et al. | |
| 5,202,231 A | 4/1993 | Drmanac et al. | |
| 5,302,509 A | 4/1994 | Cheeseman | |
| 5,403,711 A | 4/1995 | Walder et al. | |
| 5,573,907 A | 11/1996 | Carrino et al. | |
| 5,654,142 A | 8/1997 | Kievits et al. | |
| 5,660,988 A | 8/1997 | Duck et al. | |
| 5,679,524 A | 10/1997 | Nikiforov et al. | |
| 5,723,591 A | 3/1998 | Livak et al. | |
| 5,740,341 A | 4/1998 | Oota et al. | |
| 5,766,849 A | 6/1998 | McDonough et al. | |
| 5,854,033 A | 12/1998 | Lizardi | |
| 6,027,923 A | 2/2000 | Wallace | |
| 6,210,891 B1 | 4/2001 | Nyren et al. | |
| 6,239,150 B1 | 5/2001 | Oshima et al. | |
| 6,258,568 B1 | 7/2001 | Nyren | |
| 6,277,607 B1 | 8/2001 | Tyagi et al. | |
| 6,562,579 B1 * | 5/2003 | Yu et al. | 435/7.1 |
| 6,716,576 B1 * | 4/2004 | Yu et al. | 435/6.16 |
| 2003/0012783 A1 * | 1/2003 | Kindsvogel | 424/144.1 |
| 2008/0268480 A1 * | 10/2008 | Hsu et al. | 435/7.92 |
| 2012/0264142 A1 | 10/2012 | Bloom et al. | |

FOREIGN PATENT DOCUMENTS

WO    WO-03001877 A2 *    1/2003

OTHER PUBLICATIONS

Xu et al. The expression of B-cell activating factor belonging to tumor necrosis factor superfamily (BAFF) significantly correlated with C4D in kidney allograft rejection. Transplant Proc 41(1): 112-116, 2009.*
Bloom et al. BAFF is increased in renal transplant patients following treatment with alemtuzumab. Am J Transplant 9: 1835-1845, 2009.*
Bloom et al. BAFF dysregulation in renal transplant patients treated with Campath-1H. Am J Transplant 9(Suppl 2): 226, 2009.*
Briones et al. Blys and Blys receptor expression in non-Hodgkin's lymphoma. Exp Hematol 30: 135-141, 2002.*
Choi et al. Blood 112: 1539-1542, 2008.*
Davis et al. Ztnf4 and soluble TACI receptor levels in serum and urine may reflect disease activity in patients with SLE. Arthritis Rheumat 44: S99, 2001; abstract 278.*
He et al. Abnormal high expression of BAFF in the peripheral lymphocytes of some kidney transplantation recipients and its bioactivity. Chinese J Immunol 24(10): 902-905, 2008 (abstract only).*
Mackay et al. BAFF and APRIL: a tutorial on B cell survival. Annu Rev immunol 21: 23-264, 2003.*
Sarantopoulos et al. High levels of B-cell activating factor in patients with actice chronic graft-versus-host disease. Clin Cancer Res 13: 6107-6114, 2007.*
Xu et al. Abnormal high expression of B-cell activating factor belonging to the TNF superfamily (BAFF) associated with long-term outcome in kidney transplant recipients. Transplant Proceed 41: 1552-1556, 2009.*

(Continued)

*Primary Examiner* — Bridget E Bunner
(74) *Attorney, Agent, or Firm* — Whyte Hirschboeck Dudek S.C.

(57) ABSTRACT

The invention relates to methods, compositions, and kits for detection of biomarkers. In one embodiment, the invention relates to a method for detecting AMR biomarkers in a biological sample. In another embodiment, the invention relates to a method for detecting, monitoring, diagnosing and predicting antibody mediated rejection. In yet another embodiment, the invention relates to a method for monitoring a subject for antibody mediated rejection comprising detecting BAFF or a BAFF variant in a biological sample. In still another embodiment, the invention relates to a kit for detecting BAFF in a urine sample.

8 Claims, 8 Drawing Sheets

(56) References Cited

OTHER PUBLICATIONS

Ye et al. BAFF binding to T cell-expressed BAFF-R costimulates T cell proliferation and alloresponses. Eur J Immunol 34: 2750-2759, 2004.*

Zhang et al. Cutting edge: a role for B lymphocyte stimulator in systemic lupus erythematosus. J Immunol 166: 6-10, 2001.*

Groom et al. Association of BAFF/Blys overexpression and altered B cell differentiation with Sjogren's syndrome. J Clin Invest 109(1): 59-68, 2002.*

Kayagaki et al. BAFF/Blys receptor 3 binds the B cell survival factor BAFF ligand throug a discrete surface loop and promotes processing of NF-KB2. Immunity 10: 515-524, 2002.*

Porcheray et al., B-Cell Immunity in the Context of T-Cell Tolerance after Combined Kidney and Bone Marrow Transplantation in Humans, American Journal of Transplantation 2009; 9:2126-2135.

Roedder et al., Biomarkers in solid organ transplantation: establishing personalized transplantation medicine, Genome Medicine 2011, 3:37, url: http://genomemedicine.com/content/3/6/37, 12 pages.

Written Opinion for International application No. PCT/US2010/053967 dated Jul. 6, 2011, 4 pages.

Xu et al., Abstract for: Abnormal high expression of BAFF in the peripheral lymphocytes of some kidney transplantation recipients and its potential bioactivity, Chinese journal of Immunology, v 24, n 10, p. 902-905, Oct. 20, 2008.

International Search Report for PCT App. No. PCT/US2010/053967 mailed on Jul. 6, 2011.

"The Role of B Cell Activating Factor in Antibody-Medicated Allograft Rejection," report, no author, 30 pages.

Canard B. et al, "DNA Polymerase Fluorescent Substrates with Reversible 3'-tags," Gene, vol. 148(1):1-6, Oct. 1994.

Chow S. et al., "Measurement of MAP kinase Activation By Flow Cytometry using Phospho-specific Antibodies to MEK and ERK: Potential for Pharmacodynamics Monitoring of Signal Transduction Inhibitors," (Communications in Clinical Cytometry) Cytometry, 46(2):72-78, Apr. 15, 2001.

Davis D. W., et al., "Pharmacodynarnic Analysis of Target Inhibition and Endothelial Cell Death in Tumors Treated with the Vascular Endothelial Growth Factor Receptor Antagonists SU5416 or SU6668," Clinical Cancer Res., 11:678-689, 2005.

Drmanac, R. et al., "Sequencing by Hybridization (SBH) Advantages, Achievements, and Opportunities," Advances in Biochemical Engineering/Biotechnology-Chip Technology, 77:76-101, 2002.

Eis, P.S. et al., "An Invasive Cleavage Assay for Direct Quantitation of Specific RNAs," Nat. Biotechnol, 19(7):673, Jul. 2001.

Guatelli J. C. et al,, "Isothermal, In Vitro Amplification of Nucleic Acids by a Multienzyme Reaction Modeled After Retroviral Replication," Proc. Natl. Acad. Sci. U.S.A., 87:1874-1878, Mar. 1990.

Hampson N. et al., "Directional Random Oligonucleotide Primed (DROP) Global Amplification of cDNA: Its Application to Substractive cDNA Cloning," Nucl. Acids Res. 24(23):4832-4835, Dec. 1, 1996.

Maxam & Gilbert, "A New Method for Sequencing DNA," Proc. Natl. Acad. Sci., 74:560-564, Feb. 1977.

Metzker et al., "Termination of DNA Synthesis By Novel 3'-Modified-deoxyribonucleoside 5'-Triphosphates," Nucleic Acids Research, 22(20):4259-4267, Oct. 11, 1994.

Mullis K. et al,, "Specific Enzymatic Amplification of DNA In Vitro: The Polymerase Chain Reaction," Cold Spring Harbor Symp. Quant. Biol. 51:263-273, 1986.

Ponticelli, "Calcineurin-inhibitors In Renal Transplantation. Too precious To Be Abandoned," Nephrol Dial transplant, 15:1307-1309, 2000.

Quantikine, For The Quantitative Determination of Human B Cell Activating Factor Belonging To The TNF Family (BAFF) Concentrations In Cell Culture Supernates, Serum, and Plasma, Human BAFF BLyS/TNFSF13B Immunoassay, instruction booklet, 16 pages, R&D Systems, Inc., 2008.

Sanger, F et al., "DNA Sequencing with Chain-terminating Inhibitors," Proc. Natl. Acad. Sci., 74(2):5463-5467, Dec. 1977.

Urine BAFF in Renal Transplant Patients, 2 pages (no author).

Winandy, et al., Potential of Using Anaerobically Digested Bovine Biofiber As A Fiber Source for Wood Composites, BioResources 3(4):1244-1255, 2008.

Wu, et al., "The Ligation Amplification Reaction (LAR)—Amplification of Specific DNA Sequences Using Sequential Rounds of Template-dependent Ligation," Genomics 4:560, May 1989.

* cited by examiner

DETECTION OF B-CELL ACTIVATING FACTOR AS A BIOMARKER FOR ANTIBODY MEDIATED REJECTION IN TRANSPLANT RECIPIENTS

CROSS-REFERENCE TO RELATED APPLICATIONS

This application claims priority to provisional patent application Ser. No. 61/255,953 filed on Oct. 29, 2009, and is explicitly incorporated by reference herein.

REFERENCE TO GOVERNMENT GRANT

This invention was made with United States government support awarded by the following agency: NIH Grant No. R01 AI050938-03. The United States has certain rights in this invention.

FIELD

The invention relates to the fields of cell biology. More specifically, embodiments of the invention are related to methods, compositions and kits for monitoring, detecting, predicting, and diagnosing antibody mediated rejection.

BACKGROUND

Transplants of various organs, such as the liver, kidney, lung and heart, are regularly performed as treatment for end-stage organ disease. Allograft as well as xenograft transplants have been performed. Organ transplantation is often the best replacement therapy for patients suffering from organ disease, and offers patients an improved quality of life. Although many of these grafts survive in the short term, the long term maintenance of the grafts is often poor. Two primary causes of graft failure are cell-mediated rejection (CMR) and antibody-mediated rejection.

Antibody mediated rejection (AMR) occurs in 10-15% of the renal transplant population and, unlike other forms of rejection, is frequently irreversible. Antibodies, which mediate AMR, are difficult to fully remove therapeutically and often lead to allograft sensitization of the patient. The dire cost of sensitization is an often necessary second transplant, which is prone to even higher rejection rates. Re-transplantation further reduces the donor pool, thereby, placing an undue burden on an already stressed system.

The diagnosis for AMR currently consists of a combination of invasive and expensive assays that include detection of donor specific antibody in the patients' serum as well as histological evidence obtained by biopsy. For instance, current methods for testing for AMR following renal transplant are tedious and involve detection of CD4 staining in peritubular capillaries, together with a positive post-transplantation cross-match and evidence of histologic damage. To date, there is no inexpensive, single, straightforward test that demonstrates AMR conclusively.

Therefore, it would be useful to identify methods, compositions and kits that can non-invasively and accurately determine if an individual is or will undergo AMR.

BRIEF SUMMARY

The invention relates to the identification of a biomarker, biomarkers and biomarker combinations that are useful for detecting, diagnosing, predicting and monitoring the onset or progression of antibody mediated rejection and other inflammatory conditions.

In one embodiment, the invention relates to a method comprising adding a reagent that detects an AMR biomarker to a biological sample, comparing the level of AMR biomarker in the sample to a reference value, wherein an increase or decrease in the AMR biomarker as compared to the reference value is informative.

In another embodiment, the invention relates to a method comprising adding a reagent that detects BAFF to a biological sample, comparing the amount of BAFF in the sample to a reference value, wherein an increase or decrease in the amount of BAFF as compared to the reference value is informative.

In yet another embodiment, the invention relates to a method for monitoring a subject for antibody mediated rejection comprising: detecting BAFF or a BAFF variant in a biological sample; and comparing the amount of BAFF in the biological sample to a reference value, wherein an increase in the amount of BAFF as compared to the reference value indicates the subject is experiencing antibody mediated rejection, and a similar amount or a decrease in the amount of BAFF as compared to the reference value indicates the subject is not experiencing antibody mediated rejection.

In still another embodiment, the invention relates to a method for determining the success of an allograft comprising measuring an amount of BAFF in a biological sample from a subject, comparing the amount of BAFF in the biological sample to a reference value, wherein the reference value is obtained from a sample prior to the allograft procedure, and determining the success of the allograft, wherein an increase in the amount of BAFF as compared to the reference value decreases the likelihood for a successful long-term allograft.

In another embodiment, the invention relates to a method for monitoring a subject for antibody mediated rejection comprising: detecting BAFF or a BAFF variant in a urine sample obtained from a subject who previously received an organ transplant; and comparing the amount of BAFF in the urine sample to a reference value, wherein an increase in the amount of BAFF as compared to the reference value indicates the subject is experiencing antibody mediated rejection. In another embodiment, the organ transplant is a kidney transplant.

DETAILED DESCRIPTION

Definitions

Figure 1A:
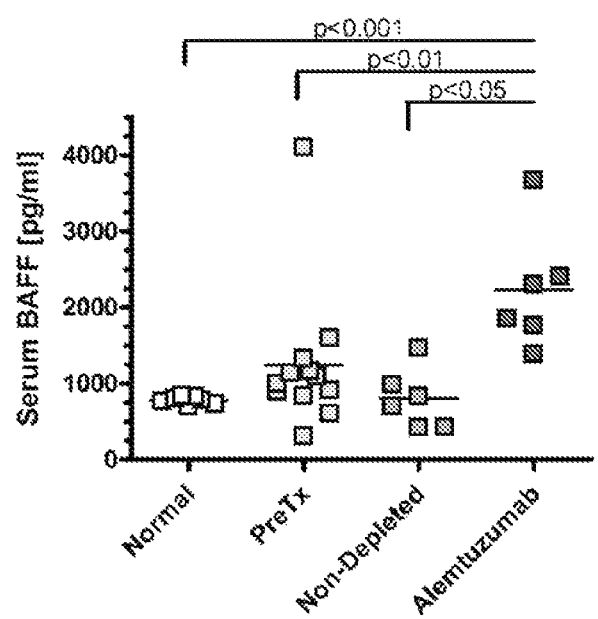
FIG. 1A is a graph reporting the serum BAFF levels measured by ELISA for the following groups: healthy control individuals ("normal"), renal transplant patients pre-transplant ("Pre-Tx"), non-depleted transplant patients treated with anti-CD25 induction therapy (measured 6 months post-transplant) ("Non-depleted"), and depleted transplant patients treated with alemtuzumab (measured at 6 months post-transplant) ("Alemtuzumab"). Statistics were performed via two-tailed t test.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values that are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "AMR biomarker" includes BAFF protein, BAFF nucleic acid sequence, BAFF mRNA, APRIL protein, APRIL nucleic acid sequence, APRIL mRNA, BAFF protein variants, BAFF nucleic acid sequence variants, BAFF mRNA variants, APRIL protein variants, APRIL nucleic acid sequence variants, and APRIL mRNA variants.

As used herein, the term "cell" or "cells," unless specifically limited to the contrary, means any somatic cell, embryonic stem (ES) cell, adult stem cell, an organ specific stem cell, nuclear transfer (NT) units, and stem-like cells. The cell or cells can be obtained from any organ or tissue. The cell or cells can be human or other animal. For example, a cell can be mouse, guinea pig, rat, cattle, horses, pigs, sheep, goats, etc. A cell also can be from non-human primates.

As used herein, the term "xenograft" means: a cell, tissue, or organ graft of a nonhuman mammalian species that normally gives rise to a rejection response in a human recipient.

As used herein, the term "rejection" encompasses an immune response with humoral and/or cellular components directed against graft or a xenograft and also encompasses non-immunological circumstances including but not limited to calcineurin inhibitor toxicity.

As used herein, the term "attenuation" means a reduction or elimination of either or both components of a rejection response.

As used herein, the term "antibody-mediated" means an immune response that directly or indirectly results from antigen-antibody interaction.

As used herein, the term "inhibit" means a reduction or elimination of the ability of an antibody to induce a rejection response.

As used herein, the term "about" refers to up to approximately a +/−10% variation from the stated value.

As used herein, the terms "a" and "an" refer to one or more unless specifically stated otherwise.

As used herein, the term "medication" includes a single drug, a combination of drugs, more than one drug, and a panel of drugs. A drug may be synthetic or natural. A drug can target a single biological pathway or multiple biological pathways.

As used herein, the term "organ" means a differentiated biological structure comprised of cells and tissues that perform a certain function or functions in an organism.

As used herein, the term "antibody" refers to an immunoglobulin molecule having a specific structure that interacts (binds) specifically with a molecule comprising the antigen used for synthesizing the antibody or with an antigen closely related to it. An antibody binds selectively or specifically to a BAFF polypeptide of the invention if the antibody binds preferentially to BAFF, e.g. has less than 25%, preferably less than 10%, preferably less than 1% cross-reactivity with a non-BAFF polypeptides. Typically, the antibody will have a binding affinity (dissociation constant (Kd) value), for the antigen of no more than $10^{-7}M$, preferably less than about $10^{-8}M$, preferably less than about $10^{-9}M$.

As used herein, the term "biological sample" means any sample derived from a subject to be assayed including but not limited to plasma, serum, blood, saliva, interstitial fluid, urine, fecal matter, synovial, cerebrospinal, lymph, seminal, amniotic, pericardial fluid and ascites.

As used herein, the term "variant" refers to polynucleotide or polypeptide sequences different from the identified sequences for the wild type polynucleotide or polypeptide, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polypeptides useful in the invention have biological activities that are the same or similar to those of the parent polypeptides or polynucleotides. The term "variant" with reference to polynucleotides and polypeptides encompasses all forms of polynucleotides and polypeptides as defined herein.

The term "variant" with reference to polypeptides also encompasses naturally occurring, recombinant and synthetically produced polypeptides. Variant polypeptide sequences preferably exhibit at least 50%, preferably at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a the wild type sequence. Identity is found over a comparison window of at least 5 amino acid positions, preferably at least 7 amino acid positions, preferably at least 10 amino acid positions, preferably at least 15 amino acid positions, preferably at least 20 amino acid positions and most preferably over the entire length of a polypeptide used in the invention.

Polypeptide variants also encompass those which exhibit a similarity to one or more of the specifically identified sequences that is likely to preserve the functional equivalence of those sequences and that could not reasonably be expected to have occurred by random chance.

As used herein, the term "mammal" or "mammalian subject" means a warm-blooded animal, e.g., from which a sample is obtained. Illustrative mammals include without limitation humans, non-human primates, pigs, cats, dogs, rodents, lapins, horses, sheep, cattle, goats and cows. The methods, assays, and kits according to the invention are particularly suited for humans.

I. Biomarkers for Antibody Mediated Rejection

In one embodiment, the invention relates to the identification of biomarkers and biomarker combinations that are useful for detecting, diagnosing, and monitoring the onset or progression of antibody mediated rejection and other inflammatory conditions.

In another embodiment, the invention relates to a method for monitoring a subject for antibody mediated rejection comprising: measuring an AMR biomarker in a biological sample, and comparing the level of the biomarker in the sample to a reference value, wherein an increase in value as compared to the reference value is indicative of antibody mediated rejection.

In still another embodiment, the invention relates to a method for monitoring a treatment in a subject comprising: detecting an AMR biomarker in a biological sample obtained from a subject receiving a treatment, and comparing the level of the biomarker in the sample to a reference value, wherein an increase or decrease in value as compared to the reference value may warrant increasing the treatment, decreasing the treatment, eliminating the treatment, and initiating a new treatment. In yet another embodiment, the treatment may be any treatment including but not limited to medication, alemtuzumab, alemtuzumab and sirolimus therapy, alemtuzumab and calcineurin inhibitors, and alemtuzumab, sirolimus therapy and calcineurin inhibitors.

In another embodiment, the expression or activity of an AMR biomarker is measured in a biological sample obtained from a subject. In another embodiment, expression or activity of an AMR biomarker is measured in vivo, e.g., using a functional imaging method. In another embodiment, expression or activity of an AMR biomarker is measured in vitro, e.g. an ELISA assay.

An expression or activity level can be qualitative or quantitative. Thus, a determination of whether a polynucleotide or polypeptide is present or absent (e.g., detectable or undetectable) constitutes determining its expression level in various embodiments while in other embodiments, a quantitative level is determined. Determining whether or not a polypeptide exhibits a particular activity (e.g., determining whether the activity is detectable or not detectable) constitutes determining the activity of the polypeptide in certain embodiments. In other embodiments, a quantitative determination of activity is performed. The phrase "expression or activity" is not intended to indicate that measurements of these parameters are mutually exclusive. A single measurement can provide information about the level of expression, activity, or both. Thus, evaluating the level of expression or activity of a protein includes evaluating one or more parameters or features that provide information about the level of expression of the protein, the activity of the protein, or both.

In still yet another embodiment, a reduced level of expression or activity of an AMR biomarker (or its absence) in a biological sample, as compared with the reference value indicates a decreased likelihood that the subject has AMR. In other embodiments, an increased level of expression or activity of the AMR biomarker (or its presence) in a biological sample, as compared with the reference value indicates an increased likelihood that the subject is experiencing AMR.

A reference value for an indicator, such as the level of expression or activity of an AMR biomarker, may be obtained in a variety of ways. In certain embodiments of the invention, the reference value is obtained by assessing the indicator in a reference sample or samples. Reference values obtained from any of a number of different reference samples can be used as a basis for comparison with values obtained from a biological test sample. The nature of the comparison and the interpretation of the result will differ depending on the nature of the reference sample.

The determination of a reference value may be performed initially and the value used thereafter for practicing the methods. Thus, it is not necessary to determine a reference value or assess a reference sample each time a particular method is practiced. However, in certain embodiments, the biological sample is compared with one or more reference or control samples known to display particular expression levels, staining patterns, etc.

In certain embodiments, the reference value is a range of values. For example, a subject may be deemed to be experiencing AMR if a value obtained for an AMR biomarker, e.g., the level of expression or activity of the AMR biomarker protein, is within a range of values or is outside a range of values. Conversely, a subject may be considered stable if a value obtained for an AMR biomarker is within a range of values or is outside a range of values.

Terms such as "compare," "comparison" and the like are used broadly herein and include determining whether a value is greater than, equal to, or less than a reference value, determining whether a value falls within a range, etc. An assessment can include determining the extent to which a value differs from a reference value or falls outside a range. An assessment can include determining whether a difference between a value and a reference value is statistically significant.

In yet another embodiment, if a test value for a biomarker for AMR differs from a reference value by a predetermined amount or proportion, the difference is considered informative in terms of evaluating the likelihood that a subject is experiencing AMR. For example, in various embodiments of the invention, if a test value is equal to approximately 0.001-1%, 1-5%, 5-10%, 10-20%, 20-30%, 30-40%, 40-50%, 50-60%, 60-70%, 70-80%, 80-90%, 90-100%, 100-110%, 110-120%, 120-130%, 130-140%, 140-150%, 150-160%, 160-170%, 170-180%, 180-190%, 190-200%, 200-250%, 250-300%, 300-400%, 400-500%, 500-1000%, and greater than 1000% of the reference value, the difference is considered informative, i.e., it indicates an increased or decreased likelihood that the subject is experiencing AMR.

In other embodiments, any difference between a test value and a reference value is considered informative. In certain embodiments, a test value that is approximately 1.1-5, 5-10, 10-15, 15-20, 20-25, 25-50 or more times as large as a reference value is considered informative. Test values that fall within any sub-range or have any specific value (specified to the tenths place) within the limits of the values set forth above are considered informative according to various embodiments of the invention. In some embodiments, the predetermined amount is independent of the reference and/or test value(s).

Some assessment methods, such as immunohistochemistry (discussed further below), utilize a scoring system, e.g., samples are assigned a score ranging from 0-3, 0-6, or 0-12, etc. When such a scoring system is used, a difference of 1 scoring unit is informative. In other embodiments, a difference of 2, 3, 4, 5, or 6 scoring units is considered informative, up to the maximum difference possible according to the scoring system.

It will be appreciated that if the methods are practiced using different techniques for assessing the indicators and/or different instruments, protocols, reagents, etc., the specific reference values used and the extent to which a difference between a test value and a reference value is informative, can differ.

The methods may be used to monitor expression or activity of the AMR biomarker over time to determine whether it is appropriate to continue therapy for graft rejection and/or to determine whether another agent should be added to the therapeutic regimen.

In still yet another embodiment, the invention relates to a method for monitoring a subject for antibody mediated rejection comprising: measuring an AMR biomarker in a biological sample, wherein the biomarker is a member of the tumor necrosis factor ligand family, and comparing the level of the biomarker in the sample to a reference value, wherein an increase or decrease in value as compared to the reference value is informative. In another embodiment, the TNF ligand family member is any member of the TNF ligand family including but not limited to TNF, FasL, lymphotoxin-α, lymphotoxin-β, TRAIl/APO-2L, CD27L, CD30L,CD40L, 4-1BBL, OX40L, TRANCE/RANKL, LIGHT, TWEAK, and TL1. TNF family members are synthesized as type II transmembrane precursors. The extracellular domain can be cleaved by metalloproteinases to form soluble cytokines. Both the extracellular domain and the soluble cytokines can be used by the methods, kits and compositions of the invention.

In still yet another embodiment, the invention relates to a method for monitoring a subject for antibody mediated rejection comprising: detecting a biomarker in a biological sample, wherein the biomarker is a chemokine, and comparing the level of the biomarker in the sample to a reference value, wherein an increase or decrease in value as compared to the reference value is informative. In yet another embodiment, the chemokine includes but is not limited to a chemokine ligand, a chemokine receptor, a bound chemokine receptor, and an unbound chemokine receptor. The chemokine includes but is not limited to CC chemokines, CXC chemokines, C chemokines and $CX_3C$ chemokines. In another embodiment, the chemokine is a CXC chemokine ligand including but not limited to CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17.

Chemokines are a family of small cytokines, or proteins secreted by cells. Chemokines are chemotactic cytokines and their name is derived from their ability to induce directed chemotaxis in nearby responsive cells. Proteins are classified as chemokines according to shared structural characteristics such as small size (they are all approximately 8-10 kilodaltons in size), and the presence of four cysteine residues in conserved locations that are key to forming their 3-dimensional shape. Members of the chemokine family are divided into four groups depending on the spacing of their first two cysteine residues: (1) CC chemokines; (2) CXC chemokines; (3) C chemokines; and (4) $CX_3C$ chemokines.

The CXC chemokine family is characterized by two N-terminal cysteines separated by one amino acid, represented by this name with an "X". There are 17 different CXC chemokine ligands described in mammals: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. The CXC chemokine family is divided into two categories: (1) CXC chemokines with a specific amino acid sequence (or motif) of glutamic acid-leucine-arginine (or ELR for short) immediately before the first cysteine of the CXC motif (ELR-positive), and (2) CXC chemokines without an ELR motif (ELR-negative).

ELR-positive CXC chemokines specifically induce the migration of neutrophils, and interact with chemokine receptors CXCR1 and CXCR2. An example of an ELR-positive CXC chemokine is interleukin-8 (IL-8), which induces neutrophils to leave the bloodstream and enter into the surrounding tissue. Other CXC chemokines that lack the ELR motif, such as CXCL13, tend to be chemoattractant for lymphocytes. CXC chemokines bind to CXC chemokine receptors, of which seven have been discovered to date, designated CXCR1-7

Chemokine (C-X-C motif) ligand 13 (CXCL13) is a small cytokine belonging to the CXC chemokine family that is also known as B lymphocyte chemoattractant (BLC). As its name suggests, this chemokine is selectively chemotactic for B cells belonging to both the B-1 and B-2 subsets. This chemokine is secreted by dendritic cells, and is expressed highly in the liver, spleen, lymph nodes, and gut of humans. The gene for CXCL13 is located on human chromosome 4 in a cluster of other CXC chemokines.

In T-lymphocytes, CXCL13 expression is thought to reflect a germinal center origin of the T-cell. Hence, expression of CXCL13 in T-cell lymphomas, such as Angioimmunoblastic T-cell Lymphoma, is thought to reflect a germinal center origin of the neoplastic T-cells.

In yet another embodiment, the invention relates to a method for monitoring a subject for antibody mediated rejection comprising: measuring a biomarker in a biological sample, wherein the biomarker is know to synergize with an interleukin, and comparing the level of the biomarker in the sample to a reference value, wherein an increase or decrease in value as compared to the reference value is informative. In another embodiment, the interleukin includes but is not limited to IL-15, IL-17, and IL-21.

A. B-Cell Activating Factor

In one embodiment, BAFF, a BAFF variant or a combination of BAFF and BAFF variants can be used to monitor, detect, predict and diagnosis antibody mediated rejection. BAFF is a key factor in B cell tolerance and is known to play critical roles in B-cell activation and survival. BAFF is a 285-amino acid long peptide glycoprotein and is expressed as a transmembrane protein on various cell types including monocytes, dendritic cells and bone marrow stromal cells. The transmembrane form can be cleaved from the membrane, generating a soluble protein fragment.

BAFF is the natural ligand of three unusual tumor necrosis factor receptors named BAFF-R, TACI, and BCMA, all of which have different affinities for BAFF. The receptors are expressed mainly on mature B lymphocytes (TACI is also found on a subset of T-cells and BCMA on plasma cells). TACI has the lowest affinity for BAFF but has high affinity for a protein similar to BAFF known as A Proliferation Inducing Ligand (APRIL). BCMA displays an intermediate binding phenotype interacts poorly with both BAFF and APRIL to varying degrees. Signaling through BAFF-R and BCMA stimulates B lymphocytes to undergo proliferation and to counter apoptosis. All these ligands act as heterotrimers (i.e. three of the same molecule) interacting with heterotrimeric receptors.

BAFF is the tumor necrosis factor ligand superfamily member 13B (TNFLSF13B), also known as B Lymphocyte Stimulator (BLyS) and TNF- and APOL-related leukocyte expressed ligand (TALL-1) and the Dendritic cell-derived TNF-like molecule (CD257 antigen; cluster of differentiation 257).

In one embodiment, the invention relates to a method comprising adding a reagent that detects BAFF to a biological sample, comparing the level of BAFF in the sample to a reference value and determining if the level of BAFF in the sample is above or below the reference value, wherein an increase or decrease in value is informative.

In another embodiment, the method comprises detecting BAFF and at least one additional biomarker. Any number of biomarkers can be detected including but not limited to 1, 2, 3, 4, 5, 6, 7, 8, 9, 10, 11, 12, 13, 14, 15, 16-20, 21-40, 41-80, 81-200, and greater than 200.

In another embodiment, the invention relates to a method for monitoring a subject for AMR comprising adding a reagent that detects BAFF to a biological sample, comparing the level of BAFF in the sample to a reference value and determining if the level of BAFF in the sample is above the reference value, wherein an increase in value is indicative of AMR.

In another embodiment, the invention relates to a method for monitoring a subject for an inflammatory condition comprising: detecting BAFF in a biological sample, and comparing the level of BAFF in the sample to a reference value. The inflammatory condition to be monitored using the methods of the invention can be any inflammatory condition readily known in the art and diagnosable by a clinician. Examples of inflammatory conditions suitable for monitoring using the methods of the invention include, but are not limited to, rheumatoid arthritis (RA), insulin-dependent diabetes mellitus, multiple sclerosis, myasthenia gravis, Crohn's disease, autoimmune nephritis, primary biliary cirrhosis, psoriasis, acute pancreatitis, allograph rejection, allergic inflammation, inflammatory bowel disease, septic shock, osteoporosis, osteoarthritis, and cognitive deficits induced by neuronal inflammation. In another embodiment, the inflammatory condition is one that affects the joint, i.e., involves inflammation in or around the joint. Inflammatory conditions of the joint include rheumatoid arthritis, juvenile rheumatoid arthritis, systemic lupus erythematosus (SLE), gout, psoriatic arthritis, ankylosing spondylitis, Reiter's syndrome, adult Still's disease, viral arthritis, bacterial arthritis, and tuberculous arthritis.

In yet another embodiment, the invention relates to a method for monitoring a subject for antibody mediated rejection comprising: detecting BAFF in a biological sample, and comparing the level of BAFF in the sample to a reference value, wherein an increase in value as compared to the reference value is indicative of antibody mediated rejection, and further wherein no change in value or a decrease in value indicates the subject is stable, and not experiencing signs of AMR. In another embodiment, the sample is from an individual who has received an organ transplant. In still another embodiment, the sample is from a subject who has manifested at least some form of graft rejection. In another embodiment, the sample is from an individual suspected of having graft rejection or antibody mediated rejection.

In still another embodiment, the invention relates to a method for monitoring a treatment in a subject comprising: detecting BAFF in a biological sample obtained from a subject receiving a treatment, and comparing the level of BAFF in the sample to a reference value, wherein an increase or decrease in value as compared to the reference value may warrant increasing treatment, decreasing treatment, eliminating treatment, and initiating a new treatment. In yet another embodiment, the treatment may be any treatment including but not limited to medication, alemtuzumab, alemtuzumab and sirolimus therapy, alemtuzumab and calcineurin inhibitors, and alemtuzumab, sirolimus therapy and calcineurin inhibitors.

In yet another embodiment, the transplanted organ can be any solid organ including but not limited to heart, lung, double lung transplant, heart/lung, liver, pancreas, pancreatic islet cells, small bowel, and small bowel and liver transplant.

In still another embodiment, the methods can be used to detect membrane bound BAFF or soluble BAFF.

In one embodiment, the reference value is a value obtained from a subject in the normal population or from the subject when the individual has no graft rejection. In yet another embodiment, the reference value is a value obtained from an individual who has received an organ transplant but is deemed to be stable and not experiencing any graft rejection.

In yet another embodiment, the reference value is 800 pg/ml+/−50-75 pg/ml as determined by normal individuals in the population. One of ordinary skill in the art will understand that normal values vary depending on the particular assay and the performance of the particular assay.

In another embodiment, the method further comprises diagnosing antibody mediated rejection when the level of BAFF in the sample is substantially elevated compared to a reference value, wherein the reference value is measured from a sample when the individual has no signs of antibody mediated rejection or from a sample or samples obtained from a normal individual or more than one individual in the population.

In another embodiment, the invention relates to a method for detecting antibody mediated rejection in an individual comprising measuring an amount of BAFF in a biological sample from the individual, and comparing the amount of BAFF in the sample to a reference value, wherein an increase in the level of BAFF indicates antibody mediated rejection.

In yet another embodiment, the invention relates to a method for predicting increased mortality and/or morbidity resulting from graft rejection in an individual, comprising: measuring a level of BAFF in a biological sample from the individual, comparing the level of BAFF in the biological sample to a control value in a control sample, and predicting increased mortality and/or morbidity when the level of BAFF in the sample is higher than that in healthy control subjects, such as when the level is in the top tercile or quartile or is increased by 20% or more compared to the control level in healthy subjects.

In yet another embodiment, the invention relates to a method for determining the success of an allograft in an individual comprising measuring an amount of BAFF in a biological sample from the individual who received an allograft, comparing the level of BAFF in the biological sample to the level before such an allograft procedure, and determining the success of the allograft. In some embodiments, the allograft is considered a success if the level of BAFF remains constant before and after the procedure. In specific embodiments, changes in BAFF levels may warrant changing the therapy including but not limited to increasing the dosage of current medication, decreasing the dosage of current medication, eliminating the current medication; initiating new medication, and initiating a new allograft procedure.

In still another embodiment, the invention relates to a method for monitoring alemtuzumab-treated subjects. In yet another embodiment, the invention relates to a method for monitoring alemtuzumab-treated patients for antibody mediated rejection. Alemtuzumab (Campath-1H), a potent lymphocyte depleting monoclonal antibody specific for glycoprotein CD52.

In another embodiment, the invention relates to methods and kits for monitoring alemtuzumab-treated subjects receiving maintenance sirolimus (SRL) therapy. In still another embodiment, subjects can be receiving calcineurin inhibitors (CNI) in combination with or in place of SRL.

B. A Proliferation Inducing Ligand

In another embodiment, APRIL, an APRIL variant or a combination of APRIL and APRIL variants can be used to monitor, detect, predict, and diagnosis antibody mediated rejection. APRIL, also known as TNSF13A, Tall-2, and TRDL-1, is a TNF ligand that is overexpressed by some tumors and stimulates tumor cell growth. APRIL is similar in sequence to BAFF. TACI and BCMA also bind the ligand APRIL.

In one embodiment, the invention relates to a method comprising adding a reagent that detects APRIL to a biological sample, comparing the level of APRIL in the sample to a reference value and determining if the level of APRIL in the sample is above or below the reference value, wherein an increase or decrease in value as compared to the reference value is informative.

In yet another embodiment, the invention relates to a method for monitoring a subject for antibody mediated rejection comprising: detecting APRIL in a biological sample, and comparing the level of APRIL in the sample to a reference value, wherein an increase or decrease in value as compared to the reference value is indicative of antibody mediated rejection. In one embodiment, the sample is from an individual who has received an organ transplant. In still another embodiment, the sample is from a subject who has manifested at least some form of graft rejection. In another embodiment, the sample is from an individual suspected of having graft rejection or antibody mediated rejection.

II. Methods for Detecting an AMR Biomarker

Any of a variety of methods known to those in the art can be used to detect an AMR biomarker in a biological sample or in a subject. Expression of an AMR biomarker can be assessed by a direct method, by which is meant any method that is based on detecting and optionally quantitating the protein. In other embodiments expression is assessed by detecting and optionally quantitating mRNA that encodes the protein. In other embodiments, expression is assessed by determining whether the genomic DNA of a cell or subject contains a mutation that affects expression of the protein. Typically such a mutation will be in a gene that encodes the protein, e.g., in an expression control region. The mutation may be an insertion, substitution, or deletion of one or more nucleotides. In certain embodiments, the mutation is a deletion of part or all of a gene that encodes an AMR biomarker.

Methods for detecting and optionally quantitating or measuring an AMR biomarker typically involve the use of a reagent that specifically binds, or at least preferentially binds, to an AMR biomarker. The reagent may be, e.g., an antibody, antibody fragment, aptamer, affibody, polypeptide, small molecule ligand, or the like. Any reagent that specifically binds, or at least preferentially binds, to an AMR biomarker can be used. Such reagents are referred to collectively as "binding agents." The binding agent may be labeled, e.g., with a radioactive moiety, fluorophore, colorimetric agent, enzyme, magnetically responsive atom or group, etc. In another embodiment, an AMR biomarker is detected and optionally quantitated using an immunological method. Such methods include, but are not limited to, Western blots; immunoassays, e.g., enzyme-linked immunosorbent assays (ELISA); flow cytometry; immunohistochemistry, reverse phase assays, etc. These methods are known to one of ordinary skill in the art.

In another embodiment, immunohistochemistry (IHC) can be used for detecting and optionally quantitating or measuring the level of expression of an AMR biomarker and can be performed either manually or using automatic staining instruments. Immunohistochemistry is a method that utilizes monoclonal or polyclonal antibodies to detect cells or specific epitopes. Typically the method detects a protein antigen. Methods for preparing and processing samples for IHC are known in the art. For example, a paraffin-embedded tissue (e.g. tumor tissue) can be prepared for IHC staining by deparaffinizing tissue sections with xylene followed by ethanol; hydrating in water and then PBS; unmasking the antigen by heating the slide in sodium citrate buffer; incubating sections in hydrogen peroxide; blocking in blocking solution; incubating the slide in primary antibody (e.g., antibodies that bind to a AMR biomarker, phospho-specific antibodies) and secondary antibody; and finally detecting using an ABC avidin/biotin detection system according to manufacturer's instructions. Numerous variations are possible. Antigen retrieval solutions and methods including microwave treatments, various wash buffers, etc., are known in the art. Methods may be optimized for any particular polypeptide of interest.

Immunohistochemistry protocols employ detection systems that make the epitope detectable to the naked eye, e.g., visible, or detectable to an automated detection system. Typically an antibody (or mixture of antibodies) that binds to a specific protein or other antigen is labeled with a fluorescent or luminescent compound, prosthetic group, radioactive moiety, or an enzyme, e.g., an enzyme that can convert a substrate to a visible dye. The labeled antibody is incubated with the tissue and after washing unbound antibody away, the bound antibody distribution is revealed by fluorescence microscopy or incubation with a chromogenic substrate. Alternately, the first antibody (primary antibody) can be unlabeled and a second antibody (with an attached label) that binds to the first antibody is employed to render the pattern of antibody staining detectable.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin. Examples of suitable radioactive material are $I^{125}$, $I^{131}$, $S^{35}$ and $H^3$. Suitable fluorogenic or chromogenic substrates include nitro blue tetrazolium (NBT) in combination with the phosphatase substrate 5-bromo-4-chloro-3-indolyl phosphate (BCIP), diaminobenzidine (DAB), etc.

IHC results can be qualitative, semi-quantitative, or quantitative. In another embodiment of the invention, results are presented in terms of a semi-quantitative scoring system, e.g., ranging from 0 (no staining), to 3+. The score can reflect the percentage of cells that stain, the intensity of staining, the pattern of staining, or any combination of the foregoing. In yet another embodiment, a sample can be considered "positive" or "negative." For example, a score of 1+, 2+, or 3+ can be considered positive, or 2+ and 3+ can be considered positive with 0 or 1+ being considered negative, etc. Staining in particular cells can be scored by comparing their intensity of staining with that of the same types of cells present in a control sample.

In still yet another embodiment, an automated, quantitative IHC method is used, in which a sample is assigned a score that is a numerical representation of the intensity of the immunohistochemical staining of the sample and represents the amount of the antigen to be detected that is present in the portion of the sample analyzed. The score can be an optical density (OD). Suitable automated IHC sample processing, scanning, and analysis systems are known in the art and are available, e.g., from Ventana Medical Systems. For example, the Benchmark™ system (Ventana Medical Systems, Tuscon Ariz.) performs automated sample preparation and processing. Samples can be assessed visually or optical imaging and computer analysis, e.g., using a system such as the Accumed Accell 2000 Image Analyzer, equipped with appropriate image analysis software, can be used to automatically acquire an image and provide a quantitative measurement of OD.

In another embodiment, flow cytometry is a method that may be useful for detecting and/or measuring AMR biomarker in a sample. Flow cytometry may be carried out according to standard methods. See, e.g. Chow et al., Cytometry (Communications in Clinical Cytometry) 46: 72-78 (2001).

Laser-scanning cytometry-mediated analysis (LSC) can be used in conjunction with immunofluorescence on tissue biopsy samples to quantify polypeptide expression levels (Davis, D W, et al., Clinical Cancer Res., 11:678-689, 2005).

In yet another embodiment, immunoassays including but not limited to an ELISA assay or modifications thereof, can be used to detect an AMR biomarker. Such detection techniques can be divided into (1) antibody capture assays; (2) antigen capture assays; (3) two-antibody capture assays, any of which can be configured by one of ordinary skill in the art to accomplish detection in a qualitative, semi-quantitative, or quantitative mode. One of ordinary skill in the art will be able to select an appropriate assay taking into consideration factors such as the abundance of the molecule to be detected and the relative sensitivity of different assay formats.

In another embodiment, the level of expression or activity of a protein, e.g., a AMR biomarker, is assessed by measuring the expression level of an mRNA that encodes the protein. In still another embodiment, measuring the expression level of an mRNA may include determining the presence or absence of a mutation in, or amplification of, a gene that encodes the protein. In still yet another embodiment, measuring the expression level of an mRNA may include determining the presence or absence of a mutation that affects the expression level of the protein and is located outside the gene that encodes the protein. More generally, other methods for assessing the expression or activity of a protein can include determining the existence, number, location, and/or nature of a post-translational modification such as phosphorylation, glycosylation, acetylation, etc., determining the localization of the protein, or detecting or measuring any biological or chemical activity of the protein (e.g., binding activity, enzymatic activity towards a substrate) etc. A mutation that affects the expression or activity of a protein can be a substitution, deletion, or addition of one or more nucleotides, a chromosomal abnormality such as an inversion, translocation, deletion, rearrangement, amplification, etc.

Suitable methods that may be used to detect and optionally quantitate mRNA include Northern blots, RT-PCR, cDNA or oligonucleotide microarray analysis, in situ hybridization (e.g., fluorescent in situ hybridization), etc. A number of the methods for nucleic acid detection and/or analysis make use of nucleic acid hybridization to detect a nucleic acid of interest, e.g., mRNA, cDNA, or genomic DNA. Suitable probes can readily be designed based on known sequences.

If desired, the nucleic acid of interest can be amplified using methods known in the art. Any suitable amplification method can be used, including exponential amplification, linked linear amplification, ligation-based amplification, and transcription-based amplification. An example of an exponential nucleic acid amplification method is the polymerase chain reaction (PCR) which is described, for example, in Mullis et al. Cold Spring Harbor Symp. Quant. Biol. 51:263-273 (1986); PCR Cloning Protocols: From Molecular Cloning to Genetic Engineering, Methods in Molecular Biology, White, B. A., ed., vol. 67 (1998); Mullis et al., U.S. Pat. Nos. 4,582,788 and 4,683,195. Linked linear amplification is disclosed by Wallace et al. in U.S. Pat. No. 6,027,923. Examples of ligation-based amplification are the ligation amplification reaction (LAR), taught by Wu et al. (Genomics 4:560 (1989)) and the ligase chain reaction. Hampson et al. (Nucl. Acids Res. 24(23):4832-4835, 1996) describe a directional random oligonucleotide primed (DROP) method.

Isothermal target amplification methods include transcription mediated amplification (TMA), self-sustained sequence replication (3SR), Nucleic Acid Sequence Based Amplification (NASBA), and variations thereof. (See Guatelli et al. Proc. Natl. Acad. Sci. U.S.A. 87:1874-1878 (1990); U.S. Pat. No. 5,766,849 (TMA); and U.S. Pat. No. 5,654,142 (NASBA)).

A wide variety of methods are available to detect mutations, e.g., in a AMR biomarker. Southern blots and restriction fragment analysis, etc., represent traditional methods. Mutation detection and/or sequence comparison can be performed using any of a variety of methods known in the art, e.g., amplification-based assays, hybridization assays, primer extension assays (e.g., allele-specific primer extension assays), oligonucleotide ligation assays (U.S. Pat. Nos. 5,185,243, 5,679,524 and 5,573,907), cleavage assays, heteroduplex tracking analysis (HTA) assays, etc. Examples include the Taqman assay from Applied Biosystems (U.S. Pat. No. 5,723,591). In this assay, two PCR primers flank a central probe oligonucleotide. The probe oligonucleotide contains two fluorescent moieties. During the polymerization step of the PCR process, the polymerase cleaves the probe oligonucleotide. The cleavage causes the two fluorescent moieties to become physically separated, which causes a change in the wavelength of the fluorescent emission. As more PCR product is created, the intensity of the novel wavelength increases. Cycling probe technology (CPT), which is a nucleic acid detection system based on signal or probe amplification rather than target amplification (U.S. Pat. Nos. 5,011,769, 5,403,711, 5,660,988, and 4,876,187), could also be employed. Invasive cleavage assays, e.g., Invader assays (Third Wave Technologies), described in Eis, P. S. et al., Nat. Biotechnol. 19:673, 2001, can also be used to detect mutations and allelic variants.

Assays based on molecular beacons (U.S. Pat. No. 6,277,607) or fluorescence energy transfer (FRET) may be used. Molecular beacons are oligonucleotide hairpins that undergo a conformational change upon binding to a perfectly matched template. The conformational change of the oligonucleotide increases the physical distance between a fluorophore moiety and a quencher moiety present on the oligonucleotide. This increase in physical distance causes the effect of the quencher to be diminished, thus increasing the signal derived from the fluorophore.

U.S. Pat. Nos. 5,854,033 and 6,239,150 describe compositions and a method for amplification of and multiplex detection of molecules of interest involving rolling circle replication. The method is useful for simultaneously detecting multiple specific nucleic acids in a sample. Of course direct sequencing using any available method known in the art can be used. Examples include the chain termination or dideoxynucleotide method (Sanger, et al., Proc. Natl. Acad. Sci. 74:5463-5467, 1977) and the chemical degradation method (Maxam & Gilbert, Proc. Natl. Acad. Sci. 74:560-564, 1977), of which the former has been most extensively employed, improved upon, and automated. Other sequencing approaches include pyrosequencing (see, e.g., U.S. Pat. Nos. 6,210,891 and 6,258,568; sequencing by hybridization (U.S. Pat. No. 5,202,231; Drmanac, et al., Advances in Biochemical Engineering/Biotechnology, 77:76-101, 2002), sequencing by synthesis (Melamede, U.S. Pat. No. 4,863,849; Cheeseman, U.S. Pat. No. 5,302,509; Canard et al, Gene, 148: 1-6 (1994); Metzker et al, Nucleic Acids Research, 22: 4259-4267 (1994)), and sequencing by oligonucleotide ligation and detection (U.S. Pat. No. 5,740,341).

In yet another embodiment, the AMR biomarker can be detected using Luminex analysis.

A variety of methods may be used to assess activity of a AMR biomarker. Any biological or biochemical activity of the protein can be assessed. In one embodiment, the activity is binding activity of the AMR biomarker towards BAFF-R, TACI and BCMA.

Similar methods may be employed to assay binding activity of a AMR biomarker in a sample such as a tissue biopsy specimen, or in vivo using a suitable imaging technique, e.g., an imaging technique that detects labeled molecules. According to one method, a sample, e.g., a tissue biopsy sample, is incubated in the presence of a labeled AMR biomarker. After a period of time, the sample is washed to remove unbound label and is visualized, e.g., using a fluorescence microscope, automated image acquisition system, etc. Similar scoring metrics and/or quantitative analysis can be performed as described above for INC.

Kits to Detect an AMR Biomarker:

The invention further provides kits for detecting an AMR biomarker in a biological sample. The kits also can be used for correlating the amount of AMR biomarker and the likelihood of a subject experiencing an AMR. The kit can be used for monitoring, detecting, and predicting AMR. The kit can also be used to monitor a treatment in a subject.

In one embodiment of the kit, the kit includes a positive control including but not limited to soluble BAFF and cells that express BAFF. The kit can also include a negative control including cells that lack BAFF. The kit can also include a binding partner for BAFF, such as an antibody that binds to BAFF. An example of an antibody that can be used in the kit is PE Anti-human CD257 (available from BioLegend, San Diego, Calif.).

The positive control can be any cell type that expresses BAFF including but not limited to monocytes, neutrophils, bone marrow stromal cells, astrocytes, and activated lymphocytes. The negative control can be any cell or cell line that does not express BAFF.

A secondary antibody that binds to the first antibody or to the complex of the first antibody and its antigen can be included in the kit. The secondary antibody can include a detectable label. A development reagent, such as a substrate for an antibody-linked enzyme can also be included where the secondary antibody has an enzyme conjugated to it.

The kit can be employed in laboratory settings and outside the laboratory. The kit can be adapted to be portable and for use in a patient's home. For example, the kit can be adapted to be in a format like that of home pregnancy test kits in which antibody embedded filter paper is included for use in contacting a sample from the patient. The resultant binding of the antibody with the sample could then produce a positive or negative result, or could generate a graduated result that would be compared to a representation of known results.

The kit may also include a urine collection device. In addition, the kit can include diluent comprising urine and assay diluent comprising urine.

The kit can also include instructions. The instructions may provide information on incubation times, dilution factors for various antibodies, appropriate secondary antibodies, and general information on how to perform the assays.

EXAMPLES

The following Examples are provided for illustrative purposes only. The Examples are included herein solely to aid in a more complete understanding of the described invention. The Examples do not limit the scope of the invention described or claimed herein in any fashion.

Example 1

Kidney transplantation is the primary therapy for individuals with end stage renal disease. However, the lives of allograft recipients are by no means carefree. Receiving an allograft comes with the lifetime burden of taking immunosuppressive drugs with full knowledge that these drugs do not guarantee freedom from graft rejection. While acute rejection rates have decreased in recent decades, the sobering problem of antibody-mediated rejection (AMR) persists. The generation of donor specific antibody (DSA) initiates events that result in AMR and underlies immune sensitization to the donor kidney. The often necessary therapeutic removal of alloantibody and allospecific B cells in sensitized patients is expensive and inefficient. Furthermore, sensitized patients frequently lose their graft, requiring a second transplant which is limited by a reduced donor pool and met with even higher rejection rates.

Serum samples from individuals who had received a kidney transplant were analyzed for BAFF. Forty patients and seven healthy controls were enrolled under IRB-approved protocols at the University of Wisconsin—Madison after informed consent regarding the nature of the study.

Materials

Patients

All patients were recipients of primary kidney allografts. Male or female subjects aged 18 to 75 years who had received induction with alemtuzumab, and at least 2 months of CNI therapy, MMF/EC-MPS, and prednisone were enrolled. All 40 patients were enrolled post-transplant. 26 of the 40 patients were enrolled between 2-4 months post-transplant/post-depletion.

Thirty-six of the 40 patients enrolled in the study received one 30 mg dose of alemtuzumab on the day 0 post-transplant. Four patients received two-30 mg doses of alemtuzumab but were not included in our analysis because their enrollment was a year or more post-transplant and we wished to focus on those that were enrolled early post-transplant. Steroid treatment consisted of 500 mg of methylprednisolone on day 0, 250 mg IV on day 1, and 10 mg of prednisone orally on day 3 and thereafter. Corticosteroid dosing was reduced to 5-7.5 mg/day if the subject in either treatment group remained rejection free at 6 months post-study enrolment.

Subjects were receiving maintenance MMF (i.e., 500 mg BID) or EC-MPS (i.e., 360 mg BID) at the time of study enrolment. Post-enrolment, patients were randomized for CNI withdrawal by 1 month, but continued MMF/EC-MPS dosing, as tolerated, up to a maximum of 1000/720 mg BID, respectively.

The six non-depleted patients in this study received anti-CD25 (Basiliximab, Novartis, East Hanover, N.J.) induction therapy, along with conventional long-term immunosuppression (CsA, steroids, and MMF).

Enzyme Linked Immunosorbant Assays

Blood was collected in tubes without anti-coagulant, spun at 2,000 rpm for 10 minutes. Serum was collected and frozen in liquid nitrogen long-term. BAFF serum levels were detected using a BAFF Quantikine Immunoassay following the manufacturer's protocol (R&D Systems, USA). In short, the BAFF Quantikine Immunoassay employs the quantitative sandwich enzyme immunoassay technique. A monoclonal antibody specific for BAH has been pre-coated onto a microplate. Standards and samples are pipetted into the wells and any BAFF present is bound by the immobilized antibody. After washing away any unbound substances, an enzyme-linked polyclonal antibody specific for BAFF is added to the wells. Following a wash to remove any unbound antibody-enzyme reagent, a substrate solution is added to the wells and color develops in proportion to the amount of BAFF bound in the initial step. The color development is stopped and the intensity of the color is measured. A summary of the protocol is provided below:

A. Add 100 μL of Assay Diluent RD1-72 to each well.

B. For serum/plasma samples—Add 50 μL of Standard, control, or sample per well. Cover with the adhesive strip provided. Incubate for 2 hours at room temperature C. For cell culture supernate samples—Add 75. μL of Standard, control, or sample per well. Cover with the adhesive strip provided. Incubate for 2 hours at room temperature.

D. Aspirate each well and wash, repeating the process three times for a total of four washes. Wash by filling each well with Wash Buffer (400 μL) using a squirt bottle, manifold dispenser, or autowasher. Complete removal of liquid at each step is essential to good performance. After the last wash, remove any remaining Wash Buffer by aspirating or decanting. Invert the plate and blot it against clean paper towels.

E. Add 200 μL of BAFF/BLyS Conjugate to each well. Cover with a new adhesive strip. Incubate for 2 hours at room temperature. BAFF/BLyS Conjugate is polyclonal antibody against BAFF conjugated to horseradish peroxidase with preservatives.

F. Repeat the aspiration/wash as in step 5.

G. Add 200 μL of Substrate Solution to each well. Protect from light. For serum/plasma samples—Incubate for 30 minutes at room temperature. For cell culture supernate samples—Incubate for 20 minutes at room temperature.

H. Add 50 μL of Stop Solution to each well. The color in the wells should change from blue to yellow. If the color in the wells is green or the color change does not appear uniform, gently tap the plate to ensure thorough mixing.

I. Determine the optical density of each well within 30 minutes, using a microplate reader set to 450 nm. If wavelength correction is available, set to 540 nm or 570 nm. If wavelength correction is not available, subtract readings at 540 nm or 570 nm from the readings at 450 nm. This subtraction will correct for optical imperfections in the plate. Readings made directly at 450 nm without correction may be higher and less accurate.

Standards and sera were assayed in duplicate wells. Sera from normal individuals were always run alongside patient sera.

QPCR $CD14^+$ cells were purified from frozen PBMCs using $CD14^+$ microbeads for positive selection via AutoMacs separation (Miltenyi Biotec, Auburn, Calif.). Total mRNA was purified using the SV Total RNA Isolation Kit (Promega Corporation, Madison, Wis.). PCR primers for BAFF and BAFF-R were purchased from Qiagen USA as were Quantitect SYBR Green RT-PCR kits for one step RT-QPCR. A Roche Lightcycler was used for RT-QPCR.

Flow Cytometry

PBMCs were isolated via Ficoll and stored in liquid $N_2$ until time of flow analysis. All time points were run together for each patient, and normal PBMCs were run together with patient samples for consistency. Cell surface proteins were detected by flow cytometry using standard (BD Bioscience) protocols. Labeled antibodies used are as follows: FITC anti-BAFF-R, clone 8A7 (eBioscience, San Diego, Calif.); PE-anti-TACI, clone 11H3, eBioscience; FITC-anti-BCMA, pAb, R&D Systems; FITC-anti-BAFF, clone 1D6, eBioscience; PE-anti-CD25, clone M-A251 (BD Biosciences, San Jose, Calif.); APC-anti-CD69, clone FN50, BD Biosciences; PerCP-anti-CD19, clone 4G7, BD Biosciences; APC-anti-CD14, clone M5E2, BD Biosciences; PE-anti-CD3, clone HIT3a, BD Biosciences.

Luminex Analysis for Cytokines and HLA Specific Antibodies

Fluorescent bead technology was utilized to assay 50 μl of cell culture supernatants for cytokine levels using the $T_H1/T_H2$ human cytokine 9-plex kit (Bio-Rad, Inc., Hercules, Calif.). Fluorescence was detected using the Bio-Plex 200 (Bio-Rad, Inc.). Likewise, Luminex technology was used to detect single antigen specific anti-HLA antibody for both class I and class II (LabScreen; One Lambda, Inc., Canoga Park, Calif.) for the patients with rejection episodes.

Statistical Methods

Statistical differences in serum BAFF levels between groups were determined via an unpaired two-tailed t test. Pearson correlation coefficients were generated to test whether an association exists between BAFF levels versus CD20+ B cell levels, and BAFF levels versus monocyte BAFF mRNA levels.

Results

Serum BAFF was analyzed for 3 control groups: healthy individuals, renal transplant patients day—1 pre-transplant, and non-depleted transplant patients. The latter cohort was analyzed 6-12 months after transplant and had been treated on day 0 with anti-CD25 (basiliximab) therapy and maintenance IS of CNI, MMF, and prednisone. Finally, six alemtuzumab-treated patients were chosen because they had been enrolled at 6-12 months post-transplant, and had been maintained on CNI and MMF/EC-MPS up until the time of enrollment. In this way, the maintenance immunosuppression between the non-depleted and depleted patients were comparable.

As shown in FIG. 1A, levels of serum BAFF in 7 healthy individuals ranged between 700 and 800 pg/ml with little variation (SD=49.8 pg/ml). For 12 patients pre-transplant, mean values were 1245 pg/ml (SD=226 pg/ml). Mean BAFF levels of 6 non-depleted control patients were 801 pg/ml (SD=160 pg/ml). In contrast, serum BAFF levels in 6 alemtuzumab-depleted patients were elevated to 2228 pg/ml (SD=325 pg/ml), differing significantly from healthy individuals (p=0.0005), patients pre-transplant (p=0.003), and control patients (p=0.046).

Serum BAFF levels then were analyzed to gauge whether the increases were transient or maintained long term. The majority of patients in this study (26/40) were enrolled 2-4 months post-transplant. Thus, to try and maximize the number of patients for analysis while imparting some uniformity for the post-transplant time frame, we analyzed sera that were collected at this enrollment time point, and then 24 months later (or 26-28 months post-transplant).

Figure 1B:
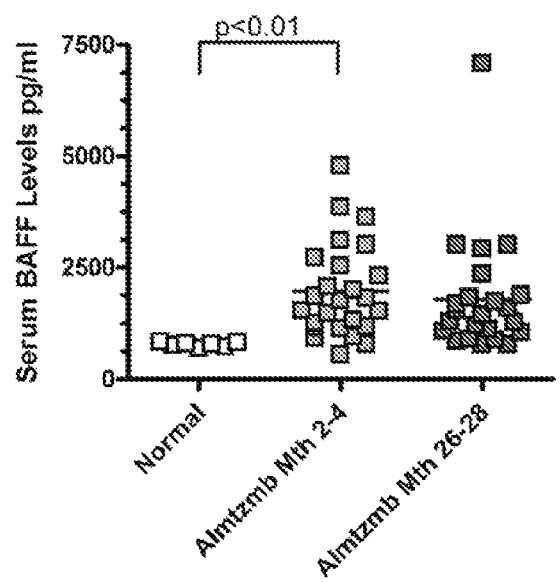
FIG. 1B is a graph reporting long term BAFF levels of alemtuzumab treated renal transplant cohorts 2-4 months post-transplant and 26-28 months later.

At 2-4 months, serum BAFF levels were increased with a mean of 1967 pg/ml (SD=1054 pg/ml) compared to a mean of 775 pg/ml for healthy controls (p=0.006, FIG. 1B). Two years later (26-28 months post-transplant) BAFF levels in alemtuzumab-depleted patients were relatively unchanged, with a mean of 1792 pg/ml (SD=1342 pg/ml, p=0.35). Importantly, at the latter time point, one-half of these patients had been withdrawn from their CNI for almost two years. However, there was no significant difference in BAFF levels between the two cohorts of patients (data not shown) suggesting that serum BAFF concentrations were not influenced by CNIs. Furthermore, BAFF levels did not correlate significantly with patient demographics such as ESRD, age, gender, donor source, PRA, individual number of HLA-A, -B, -DR mismatches, or total number of HLA-mismatches (data not shown). All patients received primary allografts and therefore the number of previous transplants was not a factor in degree of BAFF increase. Together, these data strongly suggest that alemtuzumab mediated depletion induces the BAFF increase in these patients, and that factors other than demographics determine the extent of this dysregulation.

Figure 1C:
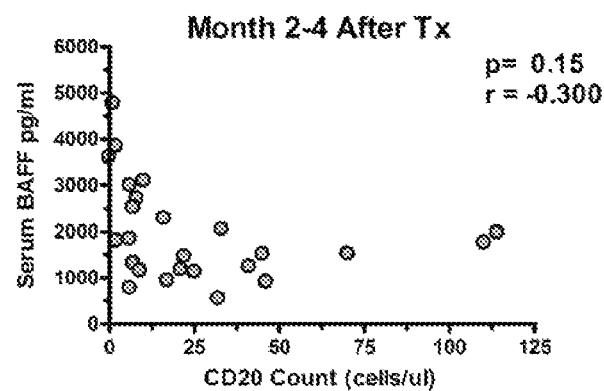
FIG. 1C is a graph reporting BAFF levels at 2-4 months post-depletion and the absolute CD20 counts in the peripheral blood. Absolute CD20 counts (X axis) at the 2-4 month time point. Pearson correlation coefficients were generated to test whether an association exists between BAFF levels and $CD20^+$ B cell levels.
Figure 1D:
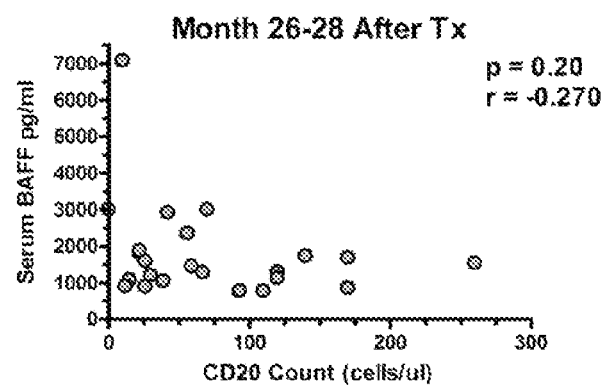
FIG. 1D is a graph reporting BAFF levels at 26-28 months post-depletion and the absolute CD20 counts in the peripheral blood. Absolute CD20 counts (X axis) at the 26-28 time point. Pearson correlation coefficients were generated to test whether an association exists between BAFF levels and $CD20^+$ B cell levels.

A principal receptor for BAFF in the peripheral blood is BAFF-R which is expressed primarily on B cells. To examine whether increased soluble BAFF in immune-depleted patients was simply a result of the lack of available BAFF-R because of B cell depletion, an investigation was performed to determine if there is an inverse correlation between. BAFF levels and absolute peripheral B cell numbers. FIG. 1C shows BAFF levels at 2-4 months and FIG. 1D reports BAFF levels at 26-28 months post-depletion and the absolute CD20 counts in the peripheral blood. At both time points, extent of B-cell depletion did not appear to correlate with BAFF levels (correlation coefficients r=0.026 for 2-4 months, r=0.060 for 26-28 months).

Figure 2A:
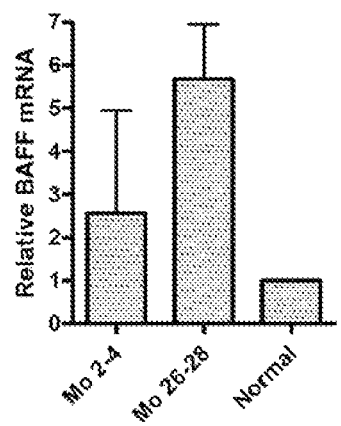
FIG. 2A is a bar graph reporting the level of BAFF mRNA in CD14+ monocytes in patients at 2-4 months post-transplant (n=8) and patients at 26-28 months post-transplant (n=4).
Figure 2B:
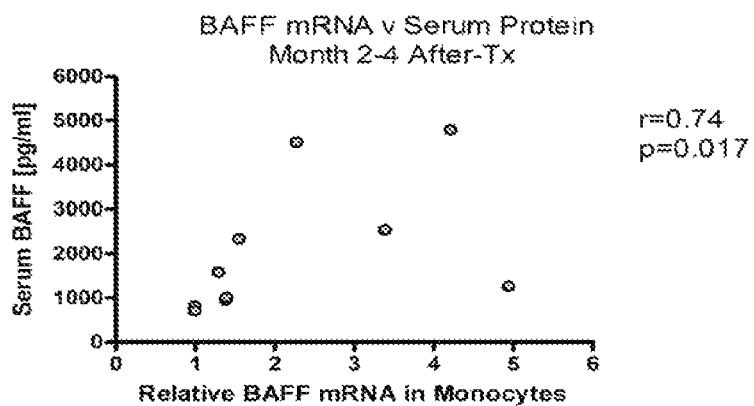
FIG. 2B is a graph reporting the correlation between BAFF mRNA levels and serum BAFF levels in patients measured at the 2-4 month time point (n=8). Pearson correlation coefficients were generated to test whether an association exists between BAFF levels and monocyte BAFF mRNA levels.

BAFF can be expressed as a membrane bound molecule on monocytes that is cleaved by a furin-like protease to produce soluble BAFF (Daridon C, Youinou P, Pers J O. BAFF, APRIL, TWE-PRIL: who's who? Autoimmun Rev 2008; 7(4):267-271). In an attempt to find a possible source for increased BAFF production, mRNA was isolated from the CD14+ monocytes of alemtuzumab patients with serum BAFF levels ranging from 1000 pg/ml to greater than 5000 pg/ml, at month 2-4 and month 26-28 post-transplant. Monocyte mRNA was also isolated from 4 normal controls. RT-QPCR was subsequently performed with BAFF primers. As shown in FIG. 2A, BAFF mRNA was expressed at 2-7 fold higher levels than normal controls. Interestingly, at the early timepoint, BAFF mRNA levels in CD14+ cells correlated with serum BAFF levels (FIG. 2B), suggesting that the dysregulation of BAFF may at least in part be due to monocytes. At the 2 year timepoint, BAFF mRNA levels did not appear to correlate with serum BAFF since patients with low serum BAFF levels had an increase in monocyte BAFF mRNA (data not shown).

Figure 2C:
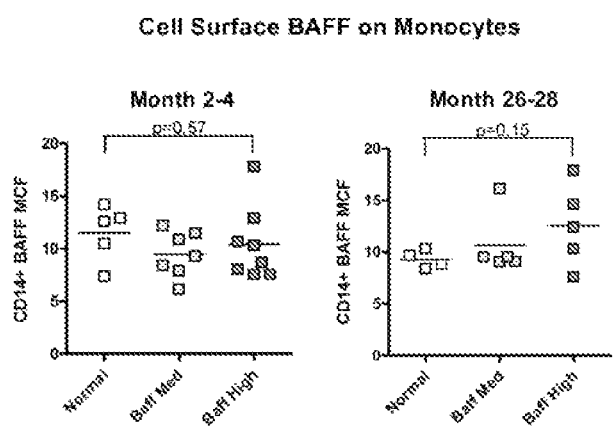
FIG. 2C is a graph reporting the amount cell surface BAFF on the monocytes of normal, $BAFF^{med}$, and $BAFF^{high}$ alemtuzumab patients at early (2-4 months) and late post-transplant (26-28 months) time points. Statistics were performed via unpaired two-tailed t test.

To determine whether increased BAFF mRNA translated to cell surface BAFF, flow cytometry on CD14+ monocytes of a subset of patients with a range of serum BAFF levels was performed. Although a shift in cell surface BAFF expression in a subset of patients was observed at the later time point (FIG. 2C), this increase was not significant overall. This suggests that the increases in BAFF protein may result mostly in the soluble and not the membrane-bound form.

Serum concentrations of BAFF are significantly increased in alemtuzumab-treated patients and the elevated BAFF levels can remain elevated long-term. Contrary to the regulation of BAFF levels in normal control individuals, serum levels of BAFF in depleted patients are unusually high and wide-range. Although alemtuzumab induction therapy appears to mediate the increase in serum BAFF levels, it is apparent that the increase is not solely due to decreased numbers of B cells. BAFF levels did not fully correlate with peripheral B cell levels, and alemtuzumab-treated patients with very similar peripheral B cell levels could have dramatically different levels of BAFF. This data suggests that BAFF production is dysregulated in these patients, and can be used to diagnose, monitor, predict and detect AMR.

BAFF levels in alemtuzumab-treated patients did not correlate significantly with patient demographics. Importantly, serum BAFF levels appear to be independent of the presence of CNIs, as those patients on CNI's did not have significantly different levels of BAFF than those withdrawn from CNI's. Likewise, MMF/EC-MPS and steroids are unlikely to have caused an increase in BAFF, as the non-depleted control patients had been maintained on these drugs as well, and did not demonstrate increases in BAFF levels. Alemtuzumab-mediated depletion increases serum BAFF concentrations.

Figure 3:
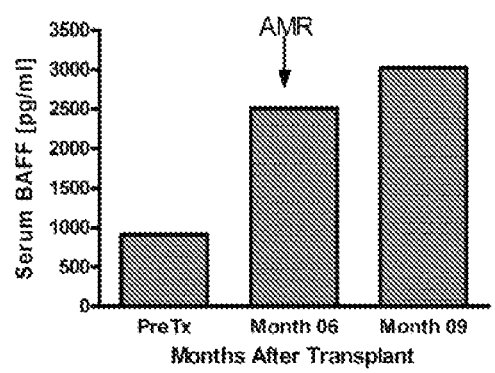
FIG. 3 is a bar graph reporting BAFF in a Basiliximab-Treated Patient with AMR

Importantly, BAFF increases are not solely a phenomenon of alemtuzumab. A patient treated with basiliximab induction therapy, and maintained on CNI, MMF, and predisone developed antibody-mediated rejection at month 6 post-transplant. The pre-transplant sera was normal for serum BAFF (900 pg/ml) but at month six, serum BAFF significantly increased to ~2500 pg/ml (FIG. 3). BAFF levels did not decrease thereafter. The patient was diagnosed with AMR at month 6. Therefore, increases in BAFF with subsequent AMR are not restricted to alemtuzumab-treated patients.

Example 2

The utility of detecting BAFF and monitoring, detecting, predicting AMR were investigated. Urine is often a desirable specimen due to the ease of handling, ease of obtaining, and the ease of shipping. In addition, urine is often free from pathogens, which greatly reduces the risk of exposure to infectious agents. Therefore, urine samples were analyzed for the ability to detect BAFF.

Methods

Sample Collection

Urine was collected from renal transplant patients during scheduled clinical visits at various times post-transplant. All samples were collected according to approved IRB protocols. All patients in the study had been given a 30 mg dose of alemtuzumab on or before the day of transplant. In the laboratory, urine was centrifuged for 10 minutes at 1200 rpm. Urine supernatants were then aliquoted and frozen at −20 degrees long term.

ELISA

At the time of analysis, urine aliquots were brought to room temperature. Using a BAFF/BLys Sandwich ELISA (Quantikine) kit from R&D Systems, Inc. (catalog number DBLYSO), urine was tested for the presence and levels of BAFF. All standards and samples were assayed in duplicate. Lyophilized standards were diluted in deionized water according to the protocol. In the original urine assay, standards were subsequently diluted serially using 2 different diluents: 1) the Calibrator Diluent RD5K supplied in the kit, and 2) urine from a healthy individual. Resulting optical densities between the two standard curves were practically identical. Aliquots of urine from the same healthy individual were used as the standard diluent. The assay diluent for sample dilution was assay diluent RD1-72. All other reagents utilized were from the BAFF ELISA kit. All other procedures and incubation times were performed according to the BAFF ELISA protocol. The optical density was determined using a microplate reader set to 450 nm.

Results

Figure 4:
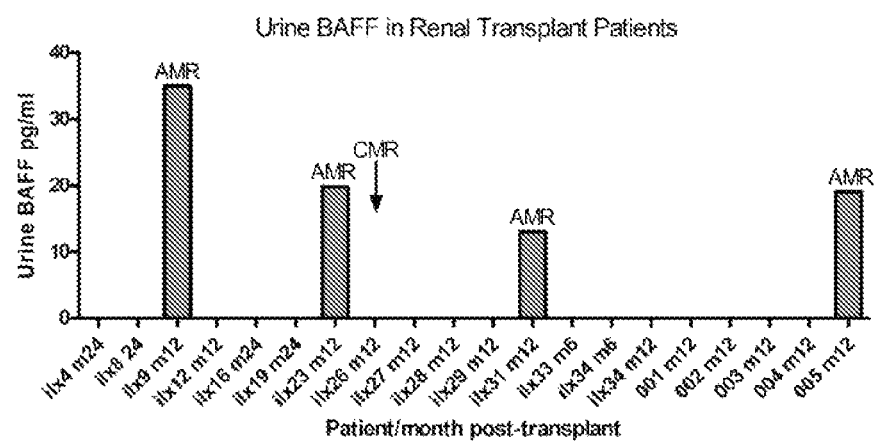
FIG. 4 is a bar graph reporting the level of BAFF in urine samples obtained from of 19 alemtuzumab-treated patients. A total of 20 samples were analyzed; subject ilX34 provided two samples: one at 6 months and one at 12 months post transplant.

As previously discussed, patients with humoral rejection had increases in serum BAFF, but not all patients with high BAFF had (perhaps yet) developed AMR. Analysis of 19 alemtuzumab-treated patients revealed that 4 patients with humoral rejection had detectable urine BAFF levels between 15-42 pg/ml at or before the time of their rejection episode (100% correlation with AMR). In contrast, fourteen patients with stable graft function (SGF) at the time of urine collection had no detectable urine BAFF (see FIG. 4) Likewise, a patient with cellular but not humoral rejection (patient ilx 26) had no detectable urine BAFF preceding, during, or following a rejection episode. In fact, the presence of BAFF in urine may be predictive of AMR, as patient ilx23 had detectable BAFF in his urine at month 12 post-transplant, and was diagnosed with AMR at month 13.

Certain patients with stable graft function displayed no detectable urine BAFF; however, serum BAFF levels were detected. Therefore, increases in serum and urine BAFF may stem from two entirely different events. High serum BAFF levels appear to correlate with the presence of serum alloantibody, but the presence of serum DSA can preclude humoral-mediated graft damage sometimes years prior to the diagnosis of AMR. In contrast, urine BAFF may be a novel indicator of an ongoing rejection episode and/or graft damage. The presence of urine BAFF may be indicative of antibody-induced kidney damage. Specifically, auto- or alloantibodies could bind and activate tubular epithelial cells or capillary endothelial cells to increase BAFF expression or secretion such that BAFF is detectable in urine.

To investigate this possibility, kidney biopsies were stained with an anti-human BAFF polyclonal antibody. Renal biopsies were taken at month 12 post-transplant. ILX8 was low serum BAFF levels and no detectable urine BAFF. ILX31 had elevated serum BAFF levels and detectable urine BAFF. Paraffin embedded biopsies were stained with a biotinylated goat anti-human BAFF polyclonal antibody with subsequent streptavidin detection.

Figure 5:
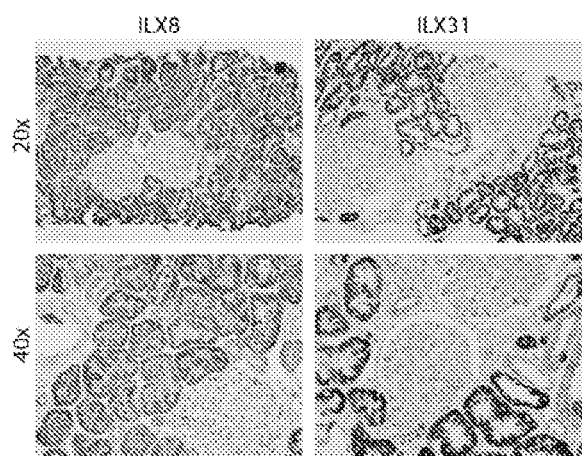
FIG. 5 is a photograph of kidney biopsies stained with an anti-human BAFF polyclonal antibody in subject. ILX8 (low serum BAFF levels and no detectable urine BAFF) and subject ILX31 (elevated serum BAFF levels and detectable urine BAFF).

The staining demonstrated that BAFF expression was relatively restricted to the kidney tubules and does not stain glomeruli (FIG. 5). Furthermore, the biopsy of patient ilx31 (who had serum DSA, AMR, and urine BAFF) appears to stain more intensely than that of ilx8 (who had no serum DSA, no AMR, and no urine BAFF). Altogether, immunohistology and urine BAFF assays suggests that humoral-mediated damage to tubules may somehow increase the expression/secretion of BAFF. BAFF in the kidney could further increase activation of any B cell infiltrates. Since BAFF is known to augment B cell chemotaxis, increases could augment the infiltration of more B cells.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations that operate according to the principles of the invention as described. Therefore, it is intended that this invention be limited only by the claims and the equivalents thereof. The disclosures of patents, references and publications cited in the application are incorporated by reference herein.

What is claimed is:

1. A method for monitoring a subject for antibody mediated rejection comprising:
   (a) comparing an amount of B-cell activating factor (BAFF) in a urine sample obtained from a subject who has received a solid organ transplant to a reference value of BAFF in urine, wherein the reference value of BAFF in urine is from the subject prior to undergoing an organ transplant, and further wherein an increase in the amount of BAFF as compared to the reference value of BAFF in urine indicates the subject is experiencing antibody mediated rejection; and
   (b) administering a medication to the subject identified in step (a) as experiencing antibody mediated rejection, wherein the medication attenuates antibody mediated rejection.

2. The method of claim 1, wherein the organ is selected from the group consisting of: liver, heart, kidney, and lung.

3. The method of claim 2, wherein the organ is a kidney.

4. A method for determining the success of an allograft comprising:
   (a) comparing an amount of B-cell activating factor (BAFF) in a urine sample obtained from a subject who has received an allograft procedure to a reference value of BAFF in urine, wherein an increase in the amount of BAFF as compared to the reference value of BAFF in urine increases the likelihood of a failed allograft; and
   (b) administering a medication to the subject identified in step (a) with an increased likelihood of a failed allograft.

5. The method of claim 4, wherein the allograft is a solid organ transplantation, and further wherein the organ is selected from the group consisting of: liver, heart, kidney, and lung.

6. The method of claim 5, wherein the organ is a kidney.

7. The method of claim 4, wherein the reference value is an average value obtained from normal subjects in a population.

8. The method of claim 4, wherein the reference value is from a subject prior to undergoing an allograft procedure.

* * * * *